(12) United States Patent
Murata et al.

(10) Patent No.: US 12,178,981 B2
(45) Date of Patent: Dec. 31, 2024

(54) DRUG ADMINISTRATION METHOD

(71) Applicant: Takeda Pharmaceutical Company Limited, Osaka (JP)

(72) Inventors: Naoyuki Murata, Kanagawa (JP); Shigeo Yanai, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1084 days.

(21) Appl. No.: 16/958,388

(22) PCT Filed: Dec. 26, 2018

(86) PCT No.: PCT/JP2018/047753
§ 371 (c)(1),
(2) Date: Jun. 26, 2020

(87) PCT Pub. No.: WO2019/131723
PCT Pub. Date: Jul. 4, 2019

(65) Prior Publication Data
US 2021/0052872 A1  Feb. 25, 2021

(30) Foreign Application Priority Data

Dec. 27, 2017  (JP) .................. 2017-252531

(51) Int. Cl.
*A61M 37/00* (2006.01)
*A61K 41/00* (2020.01)
*A61K 49/22* (2006.01)

(52) U.S. Cl.
CPC ..... *A61M 37/0092* (2013.01); *A61K 41/0047* (2013.01); *A61K 49/223* (2013.01); *A61M 2210/0693* (2013.01)

(58) Field of Classification Search
CPC ............ A61K 41/0028; A61K 41/0047; A61K 49/223; A61M 2210/0693; A61M 37/0092; A61M 2202/02; A61M 2202/04; A61M 2202/0468; A61M 2202/0488; A61M 2205/058
See application file for complete search history.

(56) References Cited

U.S. PATENT DOCUMENTS

2013/0058994 A1* 3/2013 Gabivov ............ A61K 38/1709
530/300
2014/0155813 A1  6/2014  Negishi et al.
2015/0045724 A1  2/2015  Chen et al.
2015/0250728 A1  9/2015  Murata et al.
2017/0189943 A1  7/2017  Murata et al.

FOREIGN PATENT DOCUMENTS

WO  WO-2012/153635 A1  11/2012
WO  WO-2015/182647 A1  12/2015
WO  WO-2017/178954 A1  10/2017
WO  WO-2017/210612 A1  12/2017

OTHER PUBLICATIONS

Bing et al., "Blood-Brain Barrier (BBB) Disruption Using a Diagnostic Ultrasound Scanner and Definity in Mice," Ultrasound in Medicine and Biology, 2009, 35(8):1298-1308.
"World First: Blood Brain Barrier Opened Non-Invasively to Deliver Chemotherapy," Sunnybrook Health Sciences Centre, Nov. 8, 2015, 3 pages, http://sunnybrook.ca/media/item.asp?i=1351.
Abdalkader et al., "The development of mechanically formed stable nanobubbles intended for sonoporation-mediated gene transfection," Drug Delivery, Feb. 6, 2017, 24(1):320-327.
Carpentier et al., "Clinical trial of blood-brain barrier disruption by pulsed ultrasound," Science Translational Medicine, Jun. 15, 2016, 8(343):343re2.
Fuchigami et al., "Evaluation of pharmacokinetics in the brain in brain-oriented DDS by ultrasonic responsive nanobubbles," Nagasaki University, 271-pm06 Abstracts of the 137th Annual Meeting of the Pharmaceutical Society of Japan, Mar. 2017, with English translation.
Leinenga et al., "Ultrasound treatment of neurological diseases—current and emerging applications," Nature Reviews—Neurology, Mar. 2016, 12:161-174.
Negishi et al., "Development of Gene Delivery System into Skeletal Muscles by Bubble Liposomes and Ultrasound," Yakugaku Zasshi, 2010, 130(11):1489-1496.

* cited by examiner

*Primary Examiner* — Shefali D Patel
(74) *Attorney, Agent, or Firm* — Foley & Lardner LLP

(57) ABSTRACT

The present disclosure provides a safer novel opening system with highly broad utility for a blood-brain barrier (BBB), the opening system containing a combination of (1) nano-bubble water or nano-bubble aqueous solution containing nano-bubbles having an average diameter of not more than 200 nm, and (2) an ultrasound generating apparatus; a method for opening a BBB, including using the nano-bubble water or nano-bubble aqueous solution, and an ultrasound; and a method for increasing BBB permeability of a drug, including using the nano-bubble water or nano-bubble aqueous solution, and an ultrasound.

20 Claims, No Drawings

DRUG ADMINISTRATION METHOD

CROSS-REFERENCE TO RELATED APPLICATIONS

This application is the U.S. National Stage of PCT/JP2018/047753, filed Dec. 26, 2018, which claims priority to JP 2017-252531, filed Dec. 27, 2017.

TECHNICAL FIELD

The present invention relates to 1) an opening system for a blood-brain barrier (hereinafter to be abbreviated as BBB) and the like, wherein the system is composed of nano-bubble water or nano-bubble aqueous solution containing nano-bubbles having an average diameter of not more than 200 nm, and an ultrasound generating apparatus in combination, 2) a method for opening BBB or blood-tissue barrier by using nano-bubble water or nano-bubble aqueous solution containing nano-bubbles with an average diameter of not more than 200 nm, and an ultrasound, and 3) a method for increasing BBB or blood-tissue barrier permeability of a drug by using nano-bubble water or nano-bubble aqueous solution comprising nano-bubbles with an average diameter of not more than 200 nm, and an ultrasound, and the like.

BACKGROUND OF THE INVENTION

Ultrasound has been mainly used as an ultrasound imaging apparatus in the medical field. Micro-bubble serving as an ultrasound contrast agent is making an epoch-making progress in ultrasound diagnosis. Recently, it has become possible to use ultrasound for purposes other than diagnosis. For example, non-invasive cancer hyperthermic therapy by focusing ultrasonic energy on the affected part and heating only the affected part is clinically applied for hysteromyoma and prostate cancer. In addition, focusing on non-invasiveness and ease of spatial and temporal control, research is also underway to use ultrasound exposure as a tool for drug delivery system (DDS) that delivers genes and drugs to target cells.

Heretofore, as a gene delivery system for skeletal muscle in which bubble liposome and ultrasound technique are fused, a bubble liposome in which perfluoropropane is encapsulated in a polyethylene glycol-modified liposome having a particle size of about 100 to 200 nm has been reported (non-patent document 1). A therapeutic drug for Duchenne muscular dystrophy which contains bubble liposome with a specific morpholino oligomer bound on the surface as an active ingredient, and is used for a method for highly efficiently introducing the morpholino oligomer into muscle cells by administration of the drug into the muscle tissue or blood vessel, followed by ultrasound exposure to the muscle tissue from outside the body has been reported, and it has also been reported that the aforementioned bubble liposome is a PEG-liposome encapsulating perfluorohydrocarbon, and has an average particle size of 50 to 500 nm (patent document 1).

Incidentally, for a drug to migrate from the blood (or spinal fluid) to the brain parenchyma, the drug needs to pass BBB (or spinal fluid-brain barrier). BBB is formed by a tight bond between brain capillary endothelial cells (tight junction), and a glial cell. Liposoluble medicaments passively pass through the lipid membrane of endothelial cells and easily pass through BBB. However, medicaments and the like binding to proteins such as antibody and the like, nucleic acid, plasma protein do not easily pass through BBB.

Until now, various attempts have been made to increase the BBB permeability of drugs that are difficult to pass through BBB; however, they are not yet sufficient.

It has been reported that ultrasound can be used for improving BBB permeability of drugs by injecting a chemotherapeutic agent into the blood flow of malignant brain tumor patients, injecting micro-bubbles which are smaller than erythrocyte, and exposure of blood vessels in the BBB region near the tumor to low intensity ultrasound (non-patent document 2). It has also been reported that gas-encapsulated micro-bubble and ultrasound can be used for delivering drugs and genes to the brain (non-patent document 3). It has also been reported that, in patients with recurrent glioblastoma, ultrasound exposure is started when bolus administration of SonoVue microbubbles (Bracco) is started, and carboplatin is intravenously injected within 60 min after BBB release (non-patent document 4).

However, it is difficult to make conventional micro-bubbles reach deep into the tissue after administration. On the other hand, it has been reported that nano-bubbles smaller in size (about 400 nm) than those using perfluoropropane gas or nitrogen gas are obtained using phospholipid with perfluoropropane gas (non-patent document 5). Furthermore, it has been reported that transfer of 5-FU into the brain was observed for at least 24 hr when nano-bubbles and fluorouracil (5-FU) were administered in combination to ddY mice and the brain tissue is exposed to an ultrasound (non-patent document 6).

However, the above-mentioned nano-bubbles also have an average diameter of about 400 nm, and do not have sufficient ability to reach deep into the tissue. In addition, ultrasound exposure at an output intensity of 1.5 to 2.5 $W/cm^2$ which poses concerns for safety of ultrasound diagnosis leads to a problem in terms of practicality. Furthermore, the use of bubble liposome may cause problems in antigenicity due to lipid.

The present inventors have clarified that nano-bubble water containing nano-bubbles at not less than $2.0 \times 10^8$ bubbles/mL has a superior antibacterial action (patent document 2). However, the action effect of a combination of the nano-bubble water and ultrasound is completely unknown.

DOCUMENT LIST

Patent Documents patent document 1: WO 2012/153635
patent document 2: WO 2015/182647

Non-Patent Document non-patent document 1: YAKUGAKU ZASSHI 130(11) 1489-1496 (2010)
non-patent document 2: Sunnybrook (Web), http://sunnybrook.ca/media/item.asp?i=1351
non-patent document 3: NATURE REVIEWS 12 161-174 (2016)
non-patent document 4: Science Translational Medicine 8(343) 343 (2016)
non-patent document 5: Drug Delivery 24(1) 320-327 (2017)
non-patent document 6: "Evaluation of pharmacokinetics in the brain by ultrasound-responsive nano-bubbles in brain-directed DDS", Yuki Fuchigami et al., Nagasaki University, Abstracts of the 137th Annual Meeting of the Pharmaceutical Society of Japan (March 2017)

SUMMARY OF INVENTION

Technical Problem

The present invention aims to provide a safer novel BBB opening system with highly broad utility and a means for improving the BBB permeability of a drug by using same.

Solution to Problem

To achieve the above-mentioned purpose, the present inventors took note of the nano-bubble water having a superior antibacterial action, which was developed previously by the present inventors (see the above-mentioned patent document 2). The average diameter of the nano-bubbles contained in the nano-bubble water was measured to find that it has an average diameter of not more than 200 nm which is smaller than the conventional diameter. Thus, they combined the nano-bubble water and ultrasound exposure and studied the BBB permeability of drugs. As a result, it was shown that the nano-bubble water remarkably increases the BBB permeability of a drug at an output intensity of 50-500 mW/cm$^2$, which is extremely smaller than the conventional output intensity, irrespective of the molecular weight of the drug.

Based on these findings, the present inventors have further studied and completed the present invention.

That is, the present invention relates to

[1] an opening system for BBB, comprising nano-bubble water or nano-bubble aqueous solution comprising nano-bubbles having an average diameter of not more than 200 nm, and an ultrasound generating apparatus in combination (to be also referred to as "the BBB opening system of the present invention" in the present specification);

[2] the system of [1], wherein the nano-bubble comprises a gas, and a hydrophilic resin and/or one or more kinds of surfactants selected from an anionic surfactant, a non-ionic surfactant, a cationic surfactant and an amphoteric surfactant;

[3] the system of [1], wherein the nano-bubble comprises a gas, and a non-ionic surfactant and/or a hydrophilic resin;

[4] the system of [2] or [3], wherein the gas is perfluorohydrocarbon or air;

[5] the system of any of [1] to [4], wherein the nano-bubble has an average diameter of 50 nm-200 nm;

[6] the system of any of [1] to [5], wherein the nano-bubble has a d90/d10 ratio of not more than 5;

[7] the system of any of [1] to [6], wherein the nano-bubble in the nano-bubble water or nano-bubble aqueous solution has a density of not less than $2.0 \times 10^8$ bubbles/mL;

[8] the system of any of [1] to [7], wherein the ultrasound generating apparatus has an ultrasound output intensity of not more than 720 mW/cm$^2$;

[9] the system of any of [1] to [7], wherein the ultrasound generating apparatus has an ultrasound output intensity of 50-500 mW/cm$^2$ and ultrasound frequency of 0.5-10 MHz;

[10] the system of any of [1] to [9], wherein the system increases BBB permeability of a drug;

[11] the system of [10], wherein the drug is a compound that is difficult to pass BBB;

[12] a method for opening BBB, comprising using nano-bubble water or nano-bubble aqueous solution comprising nano-bubbles with an average diameter of not more than 200 nm, and an ultrasound;

[13] a method for increasing BBB permeability of a drug, comprising using nano-bubble water or nano-bubble aqueous solution comprising nano-bubbles with an average diameter of not more than 200 nm, and an ultrasound;

and the like.

Advantageous Effects of Invention

According to the BBB opening system of the present invention, it is possible to open BBB by exposure to an ultrasound at an output intensity of a level that does not exert an adverse influence on the body, and therefore, a highly safe DDS into the brain can be provided.

The BBB opening system of the present invention contains nano-bubbles with an average diameter of not more than 200 nm. The system can efficiently reach capillary (4-7.5 μm) of the brain, and can deliver nano-bubbles deep into the brain. In addition, when ultrasound exposure is performed using micro-bubbles, the BBB tight junction is opened up widely, and reconstruction thereof takes time. In the present invention using nano-bubbles with an average diameter of not more than 200 nm, it is not necessary to open the BBB tight junction widely and reconstruction thereof is performed rapidly.

Furthermore, the nano-bubbles having an average diameter of not more than 200 nm are stable for a long time in the nano-bubble water or nano-bubble aqueous solution.

In the BBB opening system of the present invention, since use of liposome is not required, addition of a special additive such as phospholipid is not necessary, production at a low cost can be realized, and the problem of antigenicity due to phospholipid does not occur.

DETAILED DESCRIPTION OF THE INVENTION

The present invention provides an opening system for BBB or spinal fluid-brain barrier (hereinafter to be also referred to as "BBB, etc."), including nano-bubble water or nano-bubble aqueous solution containing nano-bubbles having an average diameter of not more than 200 nm, and an ultrasound generating apparatus in combination (hereinafter to be also referred to as "the system of the present invention").

In the present specification, "opening of BBB, etc." means that a compound that is originally difficult to pass through BBB, etc. (for example, a compound that is water-soluble and does not diffuse passively, a compound having a large molecular weight, a compound free of a selective transporter or receptor) passes through BBB, etc. to be in a state permitting its transfer from blood (or spinal fluid) to brain parenchyma. Therefore, the system of the present invention may increase permeability of a drug through BBB, etc. by any mechanism, and examples thereof include, but are not limited to, opening a tight junction.

The biological barrier to which the system of the present invention is applied is, for example, BBB or spinal fluid-brain barrier. Considering the feature of the system that it is not spatially limited, it can also be applied to a blood-tissue barrier other than the BBB (e.g., blood-cerebrospinal fluid barrier, blood-retinal barrier, blood-spinal cord barrier etc.).

In the present specification, the "nano-bubble" only needs to contain gas, and the inside of the nano-bubble may be a vacuum. As used herein, "vacuum" means a state of a space filled with a gas having a pressure lower than the normal atmospheric pressure. Nano-bubble is composed of, for example, one or more kinds of substances selected from 1) one or more kinds of surfactants selected from an anionic surfactant, a non-ionic surfactant, a cationic surfactant and an amphoteric surfactant, 2) a hydrophilic resin and 3) electrolytes, and a gas.

Examples of the "anionic surfactant" in the present invention include sodium lauryl sulfate and the like.

Examples of the "non-ionic surfactant" in the present invention include glycerol fatty acid ester (e.g., glycerol monostearate etc.), sucrose fatty acid ester, sorbitan fatty acid ester (e.g., sorbitan monostearate, sorbitan monolaurate etc.), polyglycerin fatty acid ester, polyoxyethylene (hydrogenated) castor oil, polyoxyethylene sorbitan fatty acid ester (e.g., sorbitan polyoxyethylene lauric acid ester (e.g., polysorbate 20 etc.), polyoxyethylene sorbitan oleic acid ester (e.g., polysorbate 80 etc.) etc.), polyethylene glycol fatty acid ester, polyoxyethylene alkyl ether (e.g., polyoxyethylene lauryl ether etc.), polyoxyethylene polyoxypropylene alkyl ether (e.g., polyoxyethylene polyoxypropylene cetyl ether etc.), polyoxyethylene alkylphenyl ether (e.g., polyoxyethylene nonylphenyl ether etc.), macrogols, polyoxyethylene polyoxypropylene glycol (e.g., poloxamer 407, poloxamer 235, poloxamer 188, poloxamine etc.) and the like. Among these, polyoxyethylene sorbitan lauric acid ester (e.g., polysorbate etc.), polyoxyethylene sorbitan oleic acid ester (e.g., polysorbate 80 etc.) are preferable. Polysorbate 20 or polysorbate 80 is further preferable, and polysorbate 80 is particularly preferable.

Examples of the "cationic surfactant" in the present invention include benzalkonium chloride, benzethonium chloride, cetylpyridinium chloride, hexadecyltrimethylammonium bromide, dequalinium chloride and the like.

Examples of the "amphoteric surfactant" in the present invention include cocamidepropyl betaine, cocamidepropyl hydroxysultaine and the like.

The above-mentioned surfactants may be used alone, or two or more kinds thereof may be used in combination.

Examples of the "hydrophilic resin" in the present invention include acrylic resin (e.g., polyacrylamide, polyacryl acid, polymethyl methacrylate), vinyl resin (e.g., polyvinylpyrrolidone, poly(vinyl alcohol) (PVA), polyvinyl ethyl ether); polysaccharide (e.g., tragacanth gum, caraya gum, methylcellulose, hydroxypropylcellulose, hydroxypropylmethylcellulose, hyaluronic acid, agarose, curdlan etc.). Among these, poly(vinyl alcohol), hydroxypropylcellulose and the like are preferable. It is more preferably poly(vinyl alcohol) or the like.

The above-mentioned hydrophilic resins alone, or two or more kinds thereof may be used in combination.

Examples of the "electrolyte" in the present invention include sodium salt (e.g., sodium chloride, sodium bromide, sodium iodide, sodium fluoride, sodium hydrogen carbonate, sodium carbonate, sodium percarbonate, sodium sulfite, sodium sulfate, sodium thiosulfate etc.), calcium salt (e.g., calcium chloride, calcium sulfate etc.), magnesium salt (e.g., magnesium chloride, magnesium sulfate, magnesium oxide, magnesium peroxide, magnesium carbonate etc.) and the like. Among these, sodium chloride, calcium chloride, sodium carbonate and the like are preferable, and sodium chloride and the like are particularly preferable.

The above-mentioned electrolytes may be used alone, or two or more kinds may be used in combination.

The "nano-bubble" in the present invention is preferably a nano-bubble composed of 1) one or more kinds of surfactants selected from an anionic surfactant, a non-ionic surfactant, a cationic surfactant and an amphoteric surfactant, and/or 2) hydrophilic resin, and a gas and the like. Among these, for example, a nano-bubble composed of a non-ionic surfactant and/or a hydrophilic resin, and a gas is preferable. In addition, a nano-bubble composed of a non-ionic surfactant and a gas is also preferable. A nano-bubble composed of 1) one or two kinds selected from polysorbate 80 and polysorbate 20 and/or 2) poly(vinyl alcohol), and a gas is further preferable. A nano-bubble composed of polysorbate 80 and/or poly(vinyl alcohol), and a gas is further preferable. A nano-bubble composed of polysorbate 80 and a gas is particularly preferable.

Examples of the "gas" in the present invention include, but are not limited to, one kind or a mixture of two or more kinds selected from perfluorohydrocarbon (e.g., perfluoropropane ($C_3F_8$), perfluorobutane etc.), air, nitrogen, ozone, oxygen, argon, carbon dioxide and helium and the like. Among these, perfluorohydrocarbon (e.g., perfluoropropane, perfluorobutane etc.), air, nitrogen, ozone, oxygen, argon and the like are preferable. Perfluorohydrocarbon (e.g., perfluoropropane, perfluorobutane etc.), air and the like are more preferable. When air is used, nano-bubbles can be produced easily at a low cost. Perfluoropropane, perfluorobutane and the like are further preferable.

The "nano-bubble" in the present invention is preferably a nano-bubble composed of (A) a non-ionic surfactant and/or a hydrophilic resin and (B) one or more kinds of gas selected from perfluorohydrocarbon, air and the like. A nano-bubble composed of (A) 1) one or two kinds selected from polysorbate 80 and polysorbate 20 and/or 2) poly(vinyl alcohol) and (B) one or two kinds of gas selected from perfluorohydrocarbon and air and the like are further preferable. A nano-bubble composed of (A) polysorbate 80 and/or poly(vinyl alcohol) and (B) perfluorohydrocarbon and/or air and the like are further preferable. A nano-bubble composed of polysorbate 80 and/or poly(vinyl alcohol), and perfluorohydrocarbon is particularly preferable.

The "nano-bubble" in the present invention does not containing amphiphilic phospholipids such as liposome and the like. Accordingly, a safer preparation that does not show antigenicity can be provided.

The "nano-bubble" in the present invention has an average diameter of about not more than 200 nm. The average diameter is preferably 10 nm-200 nm, further preferably 50 nm-200 nm, more preferably 100 nm-180 nm.

The "average diameter" in the present specification means the particle size (mode diameter) corresponding to the most frequent value of distribution (maximum value of number %).

In the present specification, the "nano-bubble water" or "nano-bubble aqueous solution" means water or aqueous solution in which gas particles (nano-bubbles) having a diameter of not more than 1000 nm are stably present. The nano-bubble water or nano-bubble aqueous solution in the present invention (hereinafter to be also referred to as "nano-bubble water, etc. in the present invention") characteristically contains nano-bubbles with an average diameter of not more than about 200 nm.

In the present invention, the nano-bubbles desirably have a uniform size. For example, when the nano-bubble diameters corresponding to cumulative 10% and cumulative 90% from the smaller diameter side of the nano-bubble number-based distribution are d10 and d90, respectively, the "d90/d10 ratio" is preferably not more than 5, further preferably not more than 4.5.

In the present invention, the number of nano-bubbles contained in the nano-bubble water, etc. means the number of nano-bubbles present in 1 mL of the nano-bubble water or nano-bubble aqueous solution, which is sometimes to be referred to as "nano-bubble density" in the present specification. The number of nano-bubbles contained in the nano-bubble water, etc. in the present invention is not particularly limited. The lower limit of the "nano-bubble density" is, for example, not less than $2.0 \times 10^8$ bubbles/mL, preferably not less than $2.5 \times 10^8$ bubbles/mL. The upper limit of the "nano-bubble density" is, for example, not more than $2.0 \times 10^9$ bubbles/mL, preferably not more than $1.0 \times 10^9$ bubbles/mL. The "nano-bubble density" in the present invention is, for example, $2.0 \times 10^8$-$2.0 \times 10^9$ bubbles/mL, preferably $2.0 \times 10^8$-$1.0 \times 10^9$ bubbles/mL, further preferably $2.5 \times 10^8$-$1.0 \times 10^9$ bubbles/mL.

The nano-bubble diameter (including nano-bubble average diameter, hereinafter the same), nano-bubble number-based distribution (including d90/d10 ratio, hereinafter the same), and nano-bubble number measured by a method using scattering of laser beam based on Brownian motion (e.g., NanoSight Ltd, LM20, LM10 etc.), a method based on electric resistance change (e.g., Beckman Coulter, Multi-sizer4, etc.), a method based on laser diffraction scattering method (e.g., Shimadzu Corporation, SALD-7100H, etc.), a method using Mie scattering (e.g., NIPPON DENSHOKU INDUSTRIES CO., LTD., NP-500T etc.) and the like. The nano-bubble diameter and nano-bubble number-based distribution used in the present invention are those measured by a tracking method (tracking method) using laser beam scattering using NanoSight (instrument name LM10) manufactured by NanoSight Ltd., or in accordance therewith.

The nano-bubble diameter, nano-bubble number-based distribution and nano-bubble number may be generally measured immediately after production of nano-bubble water, etc., or measured after long-term storage. The nano-bubble diameter, nano-bubble number-based distribution and nano-bubble number of the nano-bubble water, etc. in the present invention are stably maintained for an extremely long time (e.g., about 6 months to 2 years), the nano-bubble diameter, nano-bubble number-based distribution and nano-bubble number may be measured immediately before use after sealed storage for a certain period after production of the nano-bubble water.

In the present specification, the "water" containing nano-bubbles is not particularly limited and, for example, tap water, deionized water, distilled water, sterile distilled water, purified water for injection, ultrapure water and the like can be used. For use for injection, sterile distilled water, purified water for injection and the like are preferable.

Examples of the "aqueous solution" containing nano-bubbles in the present specification include water further containing any additive generally used in the field of pharmaceutical preparation. Examples of the "additive" include one or more kinds of surfactants selected from an anionic surfactant, a non-ionic surfactant, a cationic surfactant and an amphoteric surfactant, hydrophilic resin, electrolyte, excipient, lubricant, binder, disintegrant, solubilizing agent, suspending agent, dispersing agent, isotonicity agent, buffering agent, soothing agent, antiseptic, antioxidant, colorant, sweetening agent, pH adjuster, stabilizer, acidulant, flavor, fluidizer and the like. Pharmacologically acceptable additives are preferable. One or more kinds of surfactants selected from an anionic surfactant, a non-ionic surfactant, a cationic surfactant and an amphoteric surfactant, hydrophilic resin, electrolyte and the like are further preferable. In addition to these additives, one or more kinds of additives selected from suspending agent, stabilizer, dispersing agent, isotonicity agent and the like are preferably used.

Two or more kinds of the above-mentioned additives may be used in a mixture at appropriately ratios.

These additives can also be directly dissolved in water to prepare a nano-bubble aqueous solution as long as they do not affect the generation, stability and the like of the nano-bubbles, or the nano-bubbles are generated in water free of additive to give nano-bubble water and additives are dissolved when in use to give a nano-bubble aqueous solution.

As the aqueous solution, any of a positively-charged nano-bubble aqueous solution and a negatively-charged nano-bubble aqueous solution can be used. In the method of the present invention for increasing the blood-tissue barrier permeability of a drug by using the nano-bubble aqueous solution and ultrasound, when the drug is a polymer compound, the nano-bubble aqueous solution is preferably a positively-charged nano-bubble aqueous solution. When the drug is a polymer compound, for example, the pH of the nano-bubble aqueous solution is preferably 1-4.

The production methods of nano-bubble water is roughly divided into a method including simultaneously generating micro-bubbles (gas particles having a diameter of about 1-60 n) and nano-bubbles in water, and float-separating the micro-bubbles to leave only the nano-bubbles, and a method including directly generating nano-bubbles, and the former is the mainstream at present. The former method includes a high-speed swirling flow type in which a gas is crushed by high-speed swirling to generate a large number of micro-bubbles, and the micro-bubbles are float-separated to leave nano-bubbles in water, a pressurized dissolution type in which a gas is pressurized to be dissolved at supersaturation, the solution is rapidly decompressed to generate micro-bubbles and nano-bubbles, the micro-bubbles are float-separated to leave nano-bubbles in water, and the like.

The pressurized dissolution type is preferably used as the method for producing nano-bubble water or nano-bubble aqueous solution in the present invention. For example, the following steps 1) to 3) can be mentioned; 1) in a pressurized container pressurized to about 0.2 to 0.5 MPa by a pressurization pump, a gas is forcibly dissolved in a liquid in which (i) one or more kinds of surfactants selected from an anionic surfactant, a non-ionic surfactant, a cationic surfactant and an amphoteric surfactant, (ii) a hydrophilic resin and/or (iii) electrolyte; 2) flash operation in water through a nozzle is performed to release the depressurized and supersaturated gas into the waste water as micro-bubbles or nano-bubbles, whereby a mixture of micro-bubble water and nano-bubble water is produced; 3) aeration is discontinued and the mixture is left standing to allow micro-bubbles to be naturally separated by floating. As a result, clear nano-bubble water with only nano-bubbles remaining therein is produced.

Examples of the nano-bubble generating apparatus used in producing nano-bubble water or nano-bubble aqueous solution in the present invention include pressurized dissolution type apparatus (e.g., nanoGALF™ manufactured by IDEC, OM4-MD5-045 manufactured by AURA TEC CO., LTD., micro-bubble generator manufactured by Nikuni Corpration etc.), high-speed swirling flow type apparatus (e.g., YJ manufactured by Bi-clean, micro-bubble generating apparatus manufactured by AQUA AIR, MICROBLADE manufactured by ROYAL ELECTRIC CO., LTD. etc.) and the like. As the nano-bubble generating apparatus, a pressurized dissolution type apparatus (e.g., nanoGALF™ manufactured by IDEC) is preferable.

In the present invention, one or more kinds of surfactants selected from an anionic surfactant, a non-ionic surfactant, a cationic surfactant and an amphoteric surfactant, hydrophilic resin and/or electrolyte are used for the production of nano-bubble water or nano-bubble aqueous solution, whereby the number of nano-bubbles in the above-mentioned nano-bubble water or nano-bubble aqueous solution can be increased.

The content of one or more kinds of surfactants selected from an anionic surfactant, a non-ionic surfactant, a cationic surfactant and an amphoteric surfactant, hydrophilic resin and/or electrolyte used in the present invention in water is not particularly limited. The upper limit is preferably not more than 50% (W/V), more preferably not more than 20% (W/V), further preferably not more than 10% (W/V). The lower limit is preferably not less than 0.01% (W/V), more preferably not less than 0.05% (W/V), further preferably not less than 0.1% (W/V). As used herein, (W/V) means g/mL.

When two or more kinds of the surfactant, hydrophilic resin and electrolyte are used in combination, the total amount thereof is the content in water.

The nano-bubble water, etc. in the present invention which is produced as mentioned above is tightly sealed in a vial or ampoule and preserved. The preservation is preferably performed under shading conditions. The preservation temperature is preferably not more than room temperature, and not more than 10° C. is more preferable.

The nano-bubble water or nano-bubble aqueous solution in the present invention is preferably produced in the presence of one or more kinds of surfactants selected from an anionic surfactant, a non-ionic surfactant, a cationic surfactant and an amphoteric surfactant, hydrophilic resin and/or electrolyte. Therefore, the number of nano-bubbles in nano-bubble water, etc. can be maintained at not less than $2.0 \times 10^8$ bubbles/mL for a period when maintenance of the action effect of the nano-bubble water, etc. in the present invention (e.g., opening effect on BBB, etc. when nano-bubble water, etc. and ultrasonic treatment are used in combination, effect of increasing BBB permeability drug by using nano-bubble water, etc. and ultrasound, etc.) is required (e.g., when used as a base for a drug that is desired to be delivered through BBB, etc., the effective period thereof (e.g., not less than 3 months, more preferably not less than 6 months, further preferably not less than one year)).

The nano-bubble water, etc. in the present invention can be sterilized by heating, and the number of nano-bubbles can be maintained at not less than $2.0 \times 10^8$ bubbles/mL even after heat sterilization.

When the number of nano-bubbles in the nano-bubble water, etc. in the present invention is not less than $2.0 \times 10^8$ bubbles/mL, a superior antibacterial action and a preservation effect resulting therefrom are exhibited. Therefore, they are also useful as a base for a liquid pharmaceutical preparation of a multiple administration type which is repeatedly administered from the same container for a certain period of time, for example, injection (e.g., subcutaneous injection, intravenous injection, intramuscular injection, intraperitoneal injection, drip transfusion, intracerebral injection, intracerebrospinal fluid injection, intraocular injection etc.).

The nano-bubble water, etc. in the present invention is preferably produced in the presence of one or more kinds of surfactants selected from an anionic surfactant, a non-ionic surfactant, a cationic surfactant and an amphoteric surfactant (preferably polysorbate 80 and/or polysorbate 20, further preferably polysorbate 80), and the nano-bubbles in the produced nano-bubble water, etc. have a smaller average diameter and more uniform size (i.e., d90/d10 ratio is small). Therefore, a safer BBB opening effect is obtained in the BBB opening system of the present invention.

As an "ultrasound generating apparatus" used in the system of the present invention, any can be used as long as it can generate ultrasonic wave meeting conditions sufficient to open BBB, etc. when used in combination with the nano-bubble water, etc. in the present invention. For example, any apparatus conventionally used for ultrasound diagnosis in the clinical situation, a commercially available ultrasound gene transfer apparatus (e.g., Sonitron GTS (manufactured by Nepa Gene Co., Ltd.) etc.) and the like can be appropriately used.

The conditions of the "ultrasound generating apparatus" in the present invention include, for example, an ultrasound output intensity (acoustic energy passing through a unit area ($cm^2$) perpendicular to the traveling direction of sound waves in a unit time) of not less than 10 mW, preferably not less than 30 mW, more preferably not less than 50 mW. The upper limit of the output intensity is not particularly set. Considering that the system of the present invention aims to open BBB, etc. in mammals including human, a range that does not adversely affect the animals (e.g., cytotoxicity) is preferable as the upper limit. For example, the requirement of "not exceeding 720 $mW/cm^2$" (same as the upper limit of Track 3 of US FDA) was added to the third party certification criteria (2005) of the revised Pharmaceutical Affairs Law, and ultrasound diagnosis apparatuses in Japan are controlled so as not to exceed the upper limit. Thus, the upper limit of the ultrasound output intensity in the system of the present invention is preferably 720 $mW/cm^2$. The ultrasound output intensity is preferably 50-720 $mW/cm^2$, further preferably 50-500 $mW/cm^2$. The ultrasound output intensity used for conventional gene transfer and BBB opening is significantly higher than the above-mentioned criteria for ultrasound diagnosis applications (e.g., 1.5-2.5 $W/cm^2$), thus posing a high safety risk. In the system of the present invention, the permeability of a drug through BBB, etc. can be remarkably increased with a small output intensity (preferably 50-500 $mW/cm^2$) regardless of the molecular weight of the drug, and it is an extremely safe drug deliver system.

As the conditions of the "ultrasound generating apparatus" in the present invention, the ultrasound frequency is not particularly limited and can be appropriately selected, for example, within the range of 0.5-10 MHz. The frequency that is widely adopted at present is about 1 MHz. However, since higher frequencies are considered to have less adverse influence on the body, the frequency can be appropriately selected within the range of 1 to 5 MHz, more preferably 1 to 3 MHz.

As the conditions for using the "ultrasound generating apparatus" in the present invention, the ultrasound exposure time is not particularly limited as long as it is sufficient to open BBB, etc., and varies depending on the ultrasound output intensity. For example, even when the output intensity is 50 $mW/cm^2$, the permeability of a drug through BBB, etc. can be increased by an exposure time of 10 seconds. The ultrasound exposure time may be, for example, 1 to 60 seconds, preferably 1 to 30 seconds, more preferably 1 to 20 seconds.

As the conditions for using the "ultrasound generating apparatus" in the present invention, for example, a combination of (i) ultrasound output intensity of 50 to 720 $mW/cm^2$ (preferably 50 to 500 $mW/cm^2$), (ii) ultrasound frequency of 0.5 to 10 MHz, and (iii) ultrasound exposure time of 1 to 60 seconds can be mentioned. Among these, a combination of (i) ultrasound output intensity of 50 to 500 mW/cm$^2$, (ii) ultrasound frequency of 1 to 5 MHz, and (iii) ultrasound exposure time of 1 to 60 seconds, and the like are preferable.

The present invention also provides a method for opening BBB, etc. by using nano-bubble water or nano-bubble aqueous solution containing nano-bubbles with an average diameter of not more than 200 nm, and ultrasound (hereinafter to be also referred to as "the opening method of the present invention"). The method includes administering the nano-bubble water, etc. in the present invention to a target to cause delivery thereof to the brain capillary (or cerebrospinal fluid), and ultrasound exposure of the brain capillary (or cerebrospinal fluid), whereby BBB, etc. are opened. Furthermore, a method for increasing the permeability of a drug through BBB, etc. using nano-bubble water or nano-bubble aqueous solution containing nano-bubbles having an average diameter of not more than 200 nm and ultrasound (hereinafter to be also referred to as "the BBB permeability increasing method of the present invention") is also provided.

As the nano-bubble water or nano-bubble aqueous solution to be used in "the opening method of the present invention" and "the BBB permeability increasing method of the present invention", the above-mentioned nano-bubble water, etc. in the present invention can be used. The ultrasound exposure in "the opening method of the present invention" and "the BBB permeability increasing method of the present invention" can be performed under conditions similar to those for the use of the ultrasound generating apparatus in the above-mentioned system of the present invention.

The target to which "the opening method of the present invention" and "the BBB permeability increasing method of the present invention" can be applied is not particularly limited as long as it is an animal with biological barriers such as BBB, etc. For example, human and other mammals (e.g., mouse, rat, rabbit, dog, cat, bovine, horse, swine, monkey etc.) can be mentioned. The means for administering the nano-bubble water, etc. in the present invention to a target is not particularly limited as long as it is an administration route capable of delivering nano-bubbles to the brain capillary (or cerebrospinal fluid). For example, as a form of injection, subcutaneous injection, intravenous injection, intramuscular injection, intraperitoneal injection, drip injection, intracerebral injection, intra-cerebrospinal fluid injection and the like can be mentioned.

The dose of the nano-bubble water, etc. in the present invention is not particularly limited as long as it is an amount sufficient to open BBB, etc. by ultrasound exposure. For example, it is an amount capable of delivering nano-bubbles such that the density of nano-bubbles in brain capillary (or cerebrospinal fluid) is $1 \times 10^8$-$10 \times 10^8$ bubbles/mL, preferably $2 \times 10^8$-$5 \times 10^8$ bubbles/mL.

The ultrasound exposure can be performed by a method similar to the method conventionally used for ultrasound diagnosis, by substituting the target region with brain capillary (or cerebrospinal fluid).

The "system of the present invention", "the opening method of the present invention" and "the BBB permeability increasing method of the present invention" can open BBB, etc. non-invasively and safely, and thus particularly useful as a drug delivery system (DDS) into the brain. Accordingly, the present invention also provides use of the system of the present invention and the opening method of the present invention for increasing the permeability of a drug through BBB, etc. (hereinafter to be also referred to as "the DDS of the present invention" and "the delivery method of the present invention", respectively).

The drug (including therapeutic drug and diagnostic agent) to which the "DDS of the present invention" and the "delivery method of the present invention" can be applied is not particularly limited as long as it is a compound capable of exerting efficacy in the brain parenchyma. Examples thereof include compounds having difficulty in passing through BBB, etc. Preferably, compounds whose therapeutically or diagnostically effective amount cannot be delivered into the brain parenchyma easily unless an artificial measure for passing through BBB, etc. is taken can be mentioned. Examples of the compound having difficulty in passing through BBB, etc. include, but are not limited to, polymer compounds [for example, nucleic acid (e.g., siRNA (e.g., FAM-siRNA, manufactured by NIPPON GENE CO., LTD.), ssRNA, shRNA, miRNA, S-oligo DNA (phosphorothioate) etc.), genes (e.g., plasmid DNA, mRNA etc.), proteins (e.g., antibody (e.g., IgG (e.g., Alexa-IgG, manufactured by Invitrogen)) etc.), polysaccharides (e.g., dextran, fluorescein isothiocyanate dextran etc.) and the like], peptide, low-molecular-weight compounds (e.g., fluorescein, fluorescein sodium etc.) and the like. Among these, polymer compound, low-molecular-weight compound and the like can be preferably mentioned. They are further preferably polymer compounds and the like. They are further preferably nucleic acid, protein and the like. They are particularly preferably nucleic acid, antibody and the like.

In "the DDS of the present invention" and "the delivery method of the present invention", the amount of the drug to be used is not particularly limited as long as the density of the nano-bubbles in nano-bubble water, etc. is within the range of the nano-bubble density described in relation to the above-mentioned "system of the present invention", and can be appropriately selected depending on the kind of drug, disease, severity and the like.

In the delivery method of the present invention, the above-mentioned drug may be mixed with the nano-bubble water, etc. in the present invention and administered to the subject as a single preparation, or they may be separately formulated and administered at the same time or at different times by the same or different routes as long as they can simultaneously coexist in the brain capillary (or cerebrospinal fluid).

When the drug and the nano-bubble water, etc. in the present invention are separately formulated, the drug can be mixed with a pharmaceutically acceptable carrier in an amount that can be tolerated by human or other mammals.

Examples of the pharmaceutically acceptable carrier include pH adjusters such as monosodium phosphate, dipotassium phosphate, disodium phosphate, monopotassium phosphate, sodium hydroxide, hydrochloric acid and the like; antibiotics such as kanamycin sulfate, erythromycin lactobionate, penicillin G potassium and the like; stabilizers such as lactose, potassium glutamate, D-sorbitol, aminoacetic acid, human serum albumin and the like; colorants such as phenol red and the like; isotonicity agents such as sodium chloride, potassium chloride and the like, and the like.

In another embodiment, a mixed solution of nano-bubbles having different average diameters is administered, and plural ultrasonic waves of different frequencies or intensities are combined to allow a drug to pass through the cell barrier in stages and be delivered to a desired part in the brain or tissue.

As another embodiment, in the case of nasal mucosal administration, nano-bubbles and a drug are allowed to coexist in a solution or suspension (or may be a powder), and ultrasound is applied, whereby the nasal mucosa absorbability and brain transferability of the drug can also be improved. Particularly, when a preparation having a good retention property at the nasal mucosal site (e.g., WO 2017/073798A1 etc.) is used, the effect of enhancing the drug absorbability and brain transferability is high.

In another embodiment, a method for improving drug delivery to nerve cells (including brain nerve cells after BBB opening) can also be provided by using nano-bubble water or nano-bubble aqueous solution containing nano-bubbles having an average diameter of not more than 200 nm and ultrasound.

The method includes administering nano-bubble water, etc. in the present invention to a subject to more efficiently deliver a drug to nerve cells, and performing ultrasound exposure to nerve cells or the like, whereby membrane permeability in the nerve cells may be improved. The cell includes both in vivo and cultured cells.

As the nano-bubble water or the nano-bubble aqueous solution used in the drug delivery improving method, the above-mentioned nano-bubble water, etc. in the present invention can be used.

The ultrasound exposure in the drug delivery improving method can be performed under the following conditions (i) to (iii) and using the above-mentioned ultrasound generating apparatus in the system of the present invention.

(I) Ultrasound output intensity: not particularly limited, and may be appropriately selected within the range of, for example, not more than 720 mW/cm$^2$, output intensity of at least 50-500 mW/cm$^2$.

(ii) Ultrasound frequency: not particularly limited, and may be appropriately selected within the range of, for example, 0.5-10 MHz, preferably 1-5 MHz, more preferably 1-3 MHz.

(iii) Ultrasound exposure time: may vary depending on the ultrasound output intensity, but is not particularly limited and is, for example, 1-60 seconds, preferably 1-30 seconds, more preferably 1-20 seconds.

The present invention is further described in the following by Reference Examples and Examples; however, the present invention is not limited to them in any sense.

In the following Reference Examples and Examples, "%" indicates weight/volume % unless otherwise specified.

EXAMPLE

Reference Example 1: Preparation of Nano-Bubble Water

Polysorbate 80 (2 g) (0.2% polysorbate 80) was dissolved in water for injection (2 L), and nano-bubble water was prepared using a nano-bubble generating apparatus (nanoGALF™ FZ1N-02) manufactured by IDEC with the following settings.
gas used for preparation: $C_3F_8$
bubble water flow about 4.0 L/min
dissolution pressure 300 KPa±5%
The prepared nano-bubble water was subjected to high-pressure vapor sterilization using an autoclave as appropriate at 121-124° C. for 30 min. After sterilization, nano-bubble average diameter, nano-bubble number and d90/d10 ratio were measured by a tracking method utilizing laser beam scattering using LM10, NanoSight Ltd.

The results are shown in Table 1.

TABLE 1

| additive | average diameter | nano-bubble number | D90/d10 ratio |
|---|---|---|---|
| polysorbate 80 (after sterilization) | 120 nm ± 16 nm | 4 × 10$^8$ bubbles/mL | 3.3 |

Reference Example 2: Preparation of Nano-Bubble Water

Polysorbate 80 (1 g) (0.05% polysorbate 80) and PVA (1 g) (0.05% PVA) were dissolved in water for injection (2 L), and nano-bubble water was prepared using a nano-bubble generating apparatus (nanoGALF™ FZ1N-02) manufactured by IDEC with the following settings.
gas used for preparation: $C_3F_8$
bubble water flow about 4.0 L/min
dissolution pressure 300 KPa±5%
The prepared nano-bubble water was subjected to high-pressure vapor sterilization using an autoclave as appropriate at 121-124° C. for 30 min. After sterilization, nano-bubble average diameter, nano-bubble number and d90/d10 ratio were measured by a tracking method utilizing laser beam scattering using MP300, NanoSight Ltd.

The results are shown in Table 2.

TABLE 2

| additive | average diameter | nano-bubble number | D90/d10 ratio |
|---|---|---|---|
| polysorbate 80/PVA (after sterilization) | 170.8 nm ± 6.9 nm | 2.0 × 10$^8$ bubbles/mL | 3.2 |

Reference Example 3: Preparation of Nano-Bubble Water

Polysorbate 80 (2 g) (0.1% polysorbate 80) was dissolved in "diluted McIlvaine buffer pH 3.0" (product name) (manufactured by FUJIFILM Wako Pure Chemical Corporation) (2 L) and nano-bubble water was prepared using a nano-bubble generating apparatus (nanoGALFM FZ1N-02) manufactured by IDEC with the following settings.
gas used for preparation: $C_3F_8$
bubble water flow about 4.0 L/min
dissolution pressure 300 KPa±5%
The prepared nano-bubble water was subjected to high-pressure vapor sterilization using an autoclave as appropriate at 121-124° C. for 30 min. After sterilization, nano-bubble average diameter, nano-bubble number and d90/d10 ratio were measured by a tracking method utilizing laser beam scattering using MS300, NanoSight Ltd.

The results are shown in Table 3.

TABLE 3

| additive | average diameter | nano-bubble number | D90/d10 ratio |
|---|---|---|---|
| polysorbate 80 (after sterilization) | 148.6 nm ± 8.5 nm | 2.11 × 10$^8$ bubbles/mL | 2.3 |

In the following Examples 1-7, the nano-bubble water [nano-bubble water (PS80)] prepared in the aforementioned Reference Example 1 was used. In addition, in Example 4, the nano-bubble water prepared in the aforementioned Reference Example 2 was used, and in Example 5, the nano-bubble water prepared in the aforementioned Reference Example 3 was used.

Example 1: BBB Permeation Experiment of Fluorescein Using BBB Kit™

D-PBS described in the protocol attached to BBB Kit™ (manufactured by PharmaCo-Cell Company Ltd., RBT-24H) was prepared. Using this D-PBS, fluorescein (fluorescein sodium manufactured by Wako Pure Chemical Industries, Code No. 213-00092) was dissolved to prepare a fluorescein stock solution. The fluorescein stock solution and the nano-bubble water (PS80) prepared in Reference Example 1 were diluted with D-PBS such that the fluorescein concentration and nano-bubble density were 1 μM and 2×10$^8$ bubbles, respectively, to prepare a culture solution (volume: 500 μL) (n=3). These culture solutions were added to the blood vessel side insert (inside: volume: 500 μL) of BBB Kit™ (manufactured by PharmaCo-Cell Company Ltd., RBT-24H), and the insert was placed in the well of the plate containing D-PBS (volume 1500 μL). Using an ultrasound gene transfer apparatus (Sonitron GTS) manufactured by Nepa Gene Co., Ltd., exposure was performed for 10 sec at frequency 1 MHz, ultrasound intensity 100 mW/cm$^2$ (n=3), 250 mW/cm$^2$ (n=3), and 500 mW/cm$^2$ (n=3). After 2 hr, the concentration of fluorescein that transferred into the culture medium in the well [brain parenchyma side (outside the insert)] of the plate was measured with a microplate reader.

The permeability coefficient (Papp) was calculated from the measured fluorescein concentration, and the intracerebral transferability of fluorescein (BBB permeability) was calculated. On the other hand, a culture medium (volume: 500 μL) was prepared (n=3) using D-PBS such that the fluorescein concentration was 1 WM, and this was used as a control. The culture medium was added to the blood vessel side insert of EBB Kit™, and 2 hr later, the concentration of fluorescein that transferred to the brain side was calculated.

Plate Reader Measurement Conditions
fluorescence wavelength: 520 nm
excitation wavelength: 480 nm
flash number: 6 times
The test results are shown in Table 4.

TABLE 4

| ultrasound exposure intensity | permeability coefficient (Papp) | standard deviation (%) |
|---|---|---|
| control | 0.574 | 0.3 |
| 100 mW/cm$^2$ | 11.2 | 2.7 |
| 250 mW/cm$^2$ | 10.6 | 4.6 |
| 500 mW/cm$^2$ | 12.7 | 0.2 |

When compared with the control, clear promotion of BBB permeability was found by ultrasound exposure at not less than 100 mW/cm$^2$.

Example 2: BBB Permeation Experiment of Dextran Using BBB Kit™

D-PBS described in the protocol attached to BBB Kit™ (manufactured by PharmaCo-Cell Company Ltd., RBT-24H) was prepared. Using this D-PBS, fluorescein isothiocyanate dextran (manufactured by Tokyo Chemical Industry Co., Ltd. Cas No. 60842-46-8; FITC dextran) was dissolved to prepare an FITC dextran stock solution. The FITC dextran stock solution and the nano-bubble water (PS80) prepared in Reference Example 1 were diluted with D-PBS such that the FITC dextran concentration and nano-bubble density were 1 μM and 2×10$^8$ bubbles, respectively, to prepare a culture solution (volume: 500 μL) (n=3). These culture solutions were added to the blood vessel side insert (inside: volume: 500 μL) of BBB Kit™ (manufactured by PharmaCo-Cell Company Ltd., RBT-24H), and the insert was placed in the well of the plate containing D-PBS (volume 1500 μL). Using an ultrasound gene transfer apparatus (Sonitron GTS) manufactured by Nepa Gene Co., Ltd., exposure was performed for 10 sec at frequency 1 MHz, ultrasound intensity 50 mW/cm$^2$ (n=3), 100 mW/cm$^2$ (n=3), and 250 mW/cm$^2$ (n=3). After 2 hr, the concentration of FITC dextran that transferred into the culture medium in the well [brain parenchyma side (outside the insert)] of the plate was measured with a microplate reader.

The permeability coefficient (Papp) was calculated from the measured FITC dextran concentration, and the intracerebral transferability of FITC dextran (BBB permeability) was calculated. On the other hand, a culture medium (volume: 500 μL) was prepared (n=3) using D-PBS such that the FITC dextran concentration was 1 μM, and this was used as a control. The culture medium was added to the blood vessel side insert of BBB Kit™, processed similarly to the above, and 2 hr later, the concentration of FITC dextran that transferred to the brain side was calculated.

Plate Reader Measurement Conditions
fluorescence wavelength: 520 nm
excitation wavelength: 494 nm
flash number: 6 times
The test results are shown in Table 5.

TABLE 5

| ultrasound exposure intensity | permeability coefficient (Papp) | standard deviation (%) |
|---|---|---|
| control | 7.68 | 0.6 |
| 50 mW/cm$^2$ | 79.9 | 1.9 |
| 100 mW/cm$^2$ | 63.1 | 1.0 |
| 250 mW/cm$^2$ | 53.4 | 0.6 |

When compared with the control, clear promotion of BBB permeability was found by ultrasound exposure at not less than 50 mW/cm$^2$.

Example 3: BBB Permeation Experiment of Nucleic Acid Using BBB Kit™

D-PBS described in the protocol attached to BBB Kit™ (manufactured by PharmaCo-Cell Company Ltd., RBT-24H) was prepared, and FAM-siRNA (manufactured by NIPPON GENE CO., LTD.) was dissolved to prepare a FAM-siRNA stock solution. The FAM-siRNA stock solution and the nano-bubble water (PS80) prepared in Reference Example 1 were diluted with D-PBS such that the FAM-siRNA concentration was 1 μM and nano-bubble density was 2×10$^8$ bubbles to prepare a culture solution (volume: 500 μL) (n=2). The culture solution was added to the blood vessel side insert (inside: volume: 500 μL) of BBB Kit™ (manufactured by PharmaCo-Cell Company Ltd., RBT-24H), and the insert was placed in the well of the plate containing D-PBS (volume 1500 μL). Using an ultrasound gene transfer apparatus (Sonitron GTS) manufactured by Nepa Gene Co., Ltd., exposure was performed for sec at frequency 1 MHz and ultrasound intensity 100 mW/cm$^2$ (n=2). After 2 hr, the concentration of FAM-siRNA that transferred into the culture medium in the well [brain parenchyma side (outside the insert)] of the plate was measured with a microplate reader.

The permeability coefficient (Papp) was calculated from the measured FAM-siRNA concentration, and the intracerebral transferability of FAM-siRNA (BBB permeability) was calculated. On the other hand, a culture medium (volume: 500 μL) was prepared (n=2) using D-PBS such that the FAM-siRNA concentration was 1 μM, and this was used as a control. The control culture medium was added to the blood vessel side insert of BBB Kit™, processed similarly to the above, and 2 hr later, the concentration of FAM-siRNA that transferred to the brain side was calculated.

Plate Reader Measurement Conditions
fluorescence wavelength: 520 nm
excitation wavelength: 494 nm
flash number: 6 times
The test results are shown in Table 6.

TABLE 6

| ultrasound exposure intensity | permeability coefficient (Papp) | standard deviation (%) |
|---|---|---|
| control | 0.7 | 0.4 |
| 100 mW/cm$^2$ | 2.3 | 0.3 |

When compared with the control, clear promotion of BBB permeability of FAM-siRNA was found by ultrasound exposure at not less than 100 mW/cm$^2$.

Example 4: BBB Permeation Experiment of Fluorescein Using BBB Kit™

D-PBS described in the protocol attached to BBB Kit™ (manufactured by PharmaCo-Cell Company Ltd., RBT-24H) was prepared, and fluorescein (fluorescein sodium manufactured by Wako Pure Chemical Industries, Ltd., code No. 213-00092) was dissolved to prepare a fluorescein stock solution. The fluorescein stock solution and the nano-bubble water prepared in Reference Example 1 were diluted with D-PBS such that the fluorescein concentration was 1 μM and nano-bubble density was 2×10$^8$ bubbles to prepare a culture solution A (volume: 500 μL) (n=2). In addition, the fluorescein stock solution and the nano-bubble water prepared in Reference Example 2 were diluted with D-PBS such that the fluorescein concentration was 1 μM and nano-bubble density was 2×10$^8$ bubbles to prepare a culture solution B (volume: 500 μL) (n=2). The above-mentioned culture solution A and culture solution B were each added to the blood vessel side insert (inside: volume: 500 μL) of BBB Kit™ (manufactured by PharmaCo-Cell Company Ltd., RBT-24H), and the insert was placed in the well of the plate containing D-PBS (volume 1500 μL). Using an ultrasound gene transfer apparatus (Sonitron GTS) manufactured by Nepa Gene Co., Ltd., exposure was performed for 10 sec at frequency 1 MHz and ultrasound intensity 100 mW/cm$^2$ (n=2). After 2 hr, the concentration of FAM-siRNA that transferred into the culture medium in the well [brain parenchyma side (outside the insert)] of the plate was measured for each with a microplate reader.

The permeability coefficient (Papp) was calculated from the measured fluorescein concentration, and the intracerebral transferability of fluorescein (BBB permeability) was calculated. On the other hand, a culture medium (volume: 500 μL) was prepared (n=2) using D-PBS such that the fluorescein concentration was 1 μM, and this was used as a control. The control culture medium was added to the blood vessel side insert of BBB Kit™, processed similarly to the above, and 2 hr later, the concentration of fluorescein that transferred to the brain side was calculated.

Plate Reader Measurement Conditions
fluorescence wavelength: 520 nm
excitation wavelength: 494 nm
flash number: 6 times
The test results are shown in Table 7.

TABLE 7

| kind of nano-bubble water/aqueous solution | permeability coefficient (Papp) | standard deviation (%) |
|---|---|---|
| control | 1.79 | 0.08 |
| culture medium A (Reference Example 1) | 11.11 | 1.58 |
| culture medium B (Reference Example 2) | 13.96 | 0.42 |

When compared with the control, clear promotion of BBB permeability of fluorescein was found by using culture medium A (Reference Example 1) and culture medium B (Reference Example 2) and ultrasound exposure at not less than 100 mW/cm$^2$.

Example 5: BBB Permeation Experiment of Antibody Using BBB Kit™

D-PBS described in the protocol attached to BBB Kit™ (manufactured by PharmaCo-Cell Company Ltd., RBT-24H) was prepared, and Alexa-IgG (manufactured by Invitrogen) was dissolved to prepare an Alexa-IgG stock solution. The Alexa-IgG stock solution and the nano-bubble water prepared in Reference Example 1 were diluted with D-PBS such that the Alexa-IgG concentration was 1 μM and nano-bubble density was 2×10$^8$ bubbles to prepare a culture solution A (volume: 500 μL) (n=2). In addition, the Alexa-IgG stock solution and the nano-bubble water prepared in Reference Example 3 were diluted with D-PBS such that the Alexa-IgG concentration was 1 μM and nano-bubble density was 2×10$^8$ bubbles to prepare a culture solution B (volume: 500 μL) (n=2). The above-mentioned culture solution A and culture solution B were each added to the blood vessel side insert (inside: volume: 500 μL) of BBB Kit™ (manufactured by PharmaCo-Cell Company Ltd., RBT-24H), and the insert was placed in the well of the plate containing D-PBS (volume 1500 μL). Using an ultrasound gene transfer apparatus (Sonitron GTS) manufactured by Nepa Gene Co., Ltd., exposure was performed for 10 sec at frequency 1 MHz and ultrasound intensity 100 mW/cm$^2$ (n=2). After 2 hr, the concentration of Alexa-IgG that transferred into the culture medium in the well [brain parenchyma side (outside the insert)] of the plate was measured for each with a microplate reader.

The permeability coefficient (Papp) was calculated from the measured Alexa-IgG concentration, and the intracerebral transferability of Alexa-IgG (BBB permeability) was calculated. On the other hand, a culture medium (volume: 500 μL) was prepared (n=2) using D-PBS such that the Alexa-IgG concentration was 1 μM, and this was used as a control. This culture medium was added to the blood vessel side insert of BBB Kit™, processed similarly to the above, and 2 hr later, the concentration of Alexa-IgG that transferred to the brain side was calculated.

Plate Reader Measurement Conditions
  fluorescence wavelength: 520 nm
  excitation wavelength: 494 nm
  flash number: 6 times
  The test results are shown in Table 8.

TABLE 8

| kind of nano-bubble water/aqueous solution | permeability coefficient (Papp) | standard deviation (%) |
|---|---|---|
| control | 2.43 | 2.3 |
| culture medium A (Reference Example 1) | 4.00 | 4.8 |
| culture medium B (Reference Example 3) | 13.95 | 1.3 |

When compared with the control, clear promotion of BBB permeability of Alexa-IgG was found by using culture medium A (Reference Example 1) and ultrasound exposure at not less than 100 mW/cm$^2$. Clear promotion of BBB permeability of Alexa-IgG was found by using culture medium B (Reference Example 3) and ultrasound exposure at not less than 100 mW/cm$^2$.

Example 6: BBB Permeation Experiment of FITC Dextran Using Rat

Using water for injection, fluorescein isothiocyanate dextran (manufactured by Tokyo Chemical Industry Co., Ltd. Cas No. 60842-46-8; FITC dextran) was dissolved to prepare an FITC dextran stock solution. Using the FITC dextran stock solution and the nano-bubble water (PS80) prepared in Reference Example 1, an administration solution was prepared such that the FITC dextran concentration was 0.5 mg/mL and nano-bubble density was 2×10$^8$ bubbles (n=3).

The administration solution (0.4 mL) was injected into the rat tail vein at 1 mL/min using an injection tube and a needle of appropriate sizes (both sterilized disposable products). Using an ultrasound gene transfer apparatus (Sonitron GTS) manufactured by Nepa Gene Co., Ltd., exposure was performed for 60 sec at frequency 1 MHz and ultrasound intensity 2 W/cm$^2$ (n=3). 3 hr later, the brain was collected, homogenized in Lysis buffer (0.1 M Tris-HCl (pH 7.8), 0.1% Triton X-100, and 2 mM EDTA), and FITC dextran was extracted. The concentration of FITC dextran in the extract was measured by a microplate reader.

The permeability coefficient (Papp) was calculated from the measured FITC dextran concentration, and the intracerebral transferability of FITC dextran (BBB permeability) was calculated. On the other hand, an administration solution with the concentration of FITC dextran in the FITC dextran stock solution of 0.5 mg/mL was prepared and used as a control (n=2). The control administration solution was processed similarly to the above, and 3 hr later, the concentration of FITC dextran that transferred to the brain side was calculated.

Plate Reader Measurement Conditions
  fluorescence wavelength: 520 nm
  excitation wavelength: 494 nm
  flash number: 6 times
  The test results are shown in Table 9.

TABLE 9

| kind of nano-bubble water/aqueous solution | permeability coefficient (Papp) | standard deviation (%) |
|---|---|---|
| control | 0.89 | 0.17 |
| Reference Example 1 | 3.36 | 0.89 |

When compared with the control, promotion of brain transferability of fluorescein isothiocyanate dextran was found by ultrasound exposure using the nano-bubble water prepared in Reference Example 1.

Example 7: Study of Tight Junction Reconstruction Using BBB Kit™

The nano-bubble water (PS80) prepared in Reference Example 1 was diluted with D-PBS to 2×10$^8$ bubbles to prepare a culture medium (n=2). The culture medium was added to the blood vessel side insert (inside: volume: 500 μL) of BBB Kit™ (manufactured by PharmaCo-Cell Company Ltd., RBT-24H), and the insert was placed in the well of the plate containing D-PBS (volume 1500 μL). Using an ultrasound gene transfer apparatus (Sonitron GTS) manufactured by Nepa Gene Co., Ltd., exposure was performed for 10 sec at frequency 1 MHz, ultrasound intensity 100 mW/cm$^2$ (n=2). For evaluation of the tight junction reconstruction thereafter, trans-epithelial electrical resistance (TEER) was measured at 0 min, 30 min, 60 min, and 120 min. A non-treatment group was used as a control.

The test results are shown in Table 10.

TABLE 10

| kind of nano-bubble water/aqueous solution | 0 min | 30 min | 60 min | 120 min |
|---|---|---|---|---|
| control | 236.7 | 126.7 | 243.7 | 228.0 |
| Reference Example 1 | 173.3 | 52.3 | 193.3 | 223.3 |

When compared with the control, a transient decrease in TEER was observed by ultrasound exposure using the nano-bubble water prepared in Reference Example 1. However, 120 min later, TEER became equivalent to TEER of the control. That is, it was shown that the BBB tight junction is rapidly reconstructed when the BBB opening system of the present invention is used.

INDUSTRIAL APPLICABILITY

The BBB opening system of the present invention can efficiently open BBB by ultrasound exposure at a low output intensity, and thus can provide a highly safe DDS into the brain. In addition, since the system contains nano-bubbles having a smaller average diameter than conventional ones, it is possible to deliver a drug deep into the brain. Furthermore, since the system does not require use of liposome, it can be manufactured at a low cost and is highly safe. From the above, the system of the present invention is extremely useful as a novel DDS of a drug that exhibits efficacy in the brain parenchyma.

This application is based on patent application No. 2017-252531 filed in Japan, the contents of which are encompassed in full herein.

The invention claimed is:

1. An opening system for a blood-brain barrier, the system comprising a combination of (a) nano-bubble water or a nano-bubble aqueous solution, said nano-bubble water or said nano-bubble aqueous solution comprising nano-bubbles having an average diameter of not more than 200 nm, and (b) an ultrasound generating apparatus, wherein the nano-bubbles consist of a gas and a non-ionic surfactant.

2. The system according to claim 1, wherein the gas is perfluorohydrocarbon or air.

3. The system according to claim 1, wherein the nano-bubbles have the average diameter of 50 nm-200 nm.

4. The system according to claim 1, wherein the nano-bubbles have a d90/d10 ratio of not more than 5, wherein the d90 is a nano-bubble diameter value corresponding to cumulative 90% from a smaller diameter side of a number-based distribution of the nano-bubbles and the d10 is a nano-bubble diameter value corresponding to cumulative 10% from the smaller diameter side of the number-based distribution of the nano-bubbles.

5. The system according to claim 1, wherein the nano-bubbles in the nano-bubble water or the nano-bubble aqueous solution have a density of not less than $2.0 \times 10^8$ bubbles/mL.

6. The system according to claim 1, wherein the ultrasound generating apparatus has an ultrasound output intensity of not more than 720 mW/cm$^2$.

7. The system according to claim 1, wherein the ultrasound generating apparatus has an ultrasound output intensity of 50-500 mW/cm$^2$ and an ultrasound frequency of 0.5-10 MHz.

8. The system according to claim 1, wherein the system increases a permeability of the blood-brain barrier for a drug.

9. The system according to claim 8, wherein the drug is a compound that is difficult to pass the blood-brain barrier.

10. The system according to claim 1, wherein the nano-bubbles do not contain phospholipid.

11. The system according to claim 1, wherein the nano-bubbles are not liposomes.

12. The system according to claim 1, wherein the nanobubble water consists of water, the non-ionic surfactant and the gas.

13. A method for opening a blood-brain barrier, the method comprising using (a) nano-bubble water or a nano-bubble aqueous solution, said nano-bubble water or said nano-bubble aqueous solution comprising nano-bubbles with an average diameter of not more than 200 nm, and (b) an ultrasound, wherein the nano-bubbles consist of a gas and a non-ionic surfactant.

14. The method according to claim 13, wherein the nano-bubbles do not contain phospholipid.

15. The method according to claim 13, wherein the nano-bubbles are not liposomes.

16. The method according to claim 13, wherein the nanobubble water consists of water, the non-ionic surfactant and the gas.

17. A method for increasing blood-brain barrier permeability of a drug, the method comprising using (a) nano-bubble water or a nano-bubble aqueous solution, said nano-bubble water or said nano-bubble aqueous solution comprising nano-bubbles with an average diameter of not more than 200 nm, and (b) an ultrasound, wherein the nano-bubbles consist of a gas and a non-ionic surfactant.

18. The method according to claim 17, wherein the nano-bubbles do not contain phospholipid.

19. The method according to claim 17, wherein the nano-bubbles are not liposomes.

20. The method according to claim 17, wherein the nanobubble water consists of water, the non-ionic surfactant and the gas.

\* \* \* \* \*